(12) United States Patent
Stemmle

(10) Patent No.: US 7,357,296 B2
(45) Date of Patent: Apr. 15, 2008

(54) METHOD AND SYSTEM FOR DECONTAMINATING MAIL

(75) Inventor: Denis J. Stemmle, Stratford, CT (US)

(73) Assignee: Pitney Bowes Inc., Stamford, CT (US)

( * ) Notice: Subject to any disclaimer, the term of this patent is extended or adjusted under 35 U.S.C. 154(b) by 153 days.

(21) Appl. No.: 09/683,417

(22) Filed: Dec. 24, 2001

(65) Prior Publication Data

US 2003/0132279 A1    Jul. 17, 2003

(51) Int. Cl.
  *A47G 29/12*    (2006.01)
(52) U.S. Cl. .......................................... 232/17; 422/24
(58) Field of Classification Search ................ 232/17, 232/45, 34; 250/492.1, 455.11; 34/275; 422/24, 186.3
See application file for complete search history.

(56) References Cited

U.S. PATENT DOCUMENTS

| | | | | |
|---|---|---|---|---|
| 1,961,700 A | * | 6/1934 | Moehler | 250/455.11 |
| 2,145,196 A | * | 1/1939 | Biggs | 62/264 |
| 2,235,296 A | * | 3/1941 | Muncheryan | 250/455.11 |
| 2,245,762 A | * | 6/1941 | Stefani et al. | 250/455.11 |
| 2,822,476 A | * | 2/1958 | Osgood | 250/455.11 |
| 3,433,949 A | * | 3/1969 | Truhan | 250/504 R |
| 4,448,750 A | * | 5/1984 | Fuesting | 422/20 |
| 4,673,914 A | * | 6/1987 | Lee | 307/10.4 |
| 5,166,528 A | * | 11/1992 | Le Vay | 250/455.11 |
| 5,459,322 A | * | 10/1995 | Warkentin | 250/455.11 |
| 5,498,394 A | * | 3/1996 | Matschke | 422/24 |
| 5,814,523 A | * | 9/1998 | Zimlich et al. | 436/174 |
| 5,920,075 A | * | 7/1999 | Whitehead | 250/492.1 |
| 6,028,315 A | * | 2/2000 | Bailey et al. | 250/455.11 |
| 6,255,103 B1 | * | 7/2001 | Tamaoki et al. | 435/303.1 |
| 6,290,906 B1 | * | 9/2001 | MacNeal | 422/30 |
| 6,646,270 B2 | * | 11/2003 | Cunningham | 250/455.11 |
| 6,878,195 B2 | * | 4/2005 | Gibson | 96/224 |
| 6,923,367 B1 | * | 8/2005 | Grossman et al. | 232/17 |
| 6,948,653 B2 | * | 9/2005 | Beckert et al. | 232/45 |
| 6,997,374 B2 | * | 2/2006 | Stradley et al. | 232/45 |
| 2002/0126008 A1 | * | 9/2002 | Lopez et al. | 340/540 |
| 2003/0127506 A1 | * | 7/2003 | Braun, Jr. | 232/31 |
| 2004/0020978 A1 | * | 2/2004 | Webb | 232/17 |
| 2004/0022668 A1 | * | 2/2004 | Kitchen | 422/22 |

FOREIGN PATENT DOCUMENTS

CN    1341456 A    *    3/2002
DE    101 53 420 A1    *    6/2002

OTHER PUBLICATIONS www.usps.com (Oct. 27, 2001).*
Astro Too Surplus Electronics—The Self Decontaminating Mailbox (Dec. 26, 2001).*
Astro Too Surplus Electronics—Equipment—New Mail_Decontamination System, undated.

* cited by examiner

*Primary Examiner*—William L. Miller
(74) *Attorney, Agent, or Firm*—George M. Macdonald; Angelo N. Chaclas

(57) ABSTRACT

A method and system for sterilizing mail is provided. A mailbox is loaded with mail and closed. A decontamination process is performed over a predetermined period of time. An indicator communicates the status of the decontamination process.

10 Claims, 5 Drawing Sheets

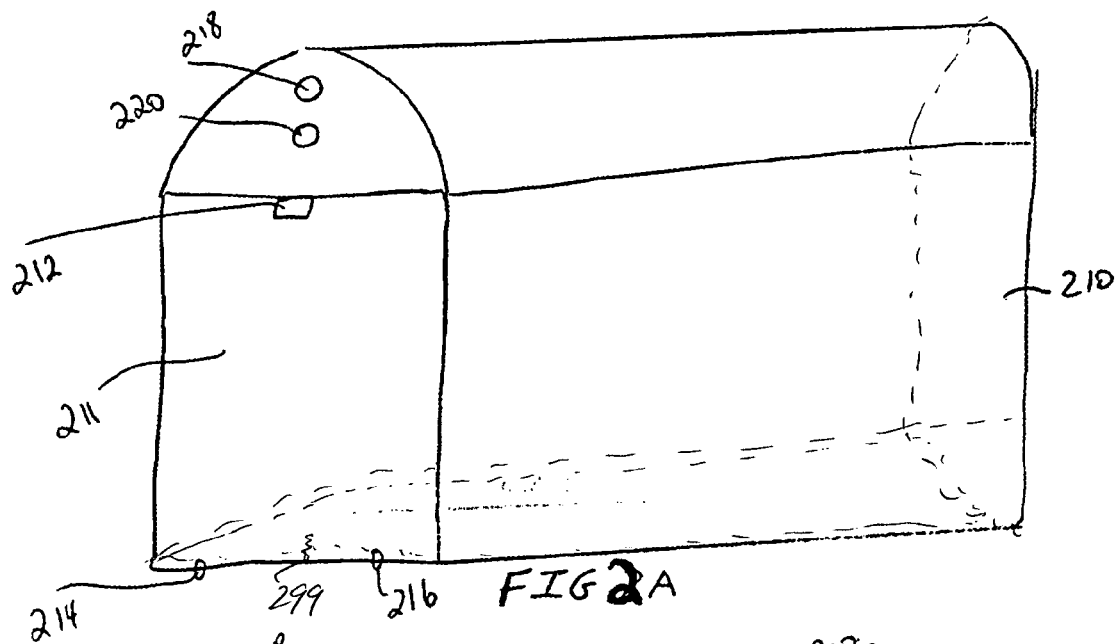
FIG 2A
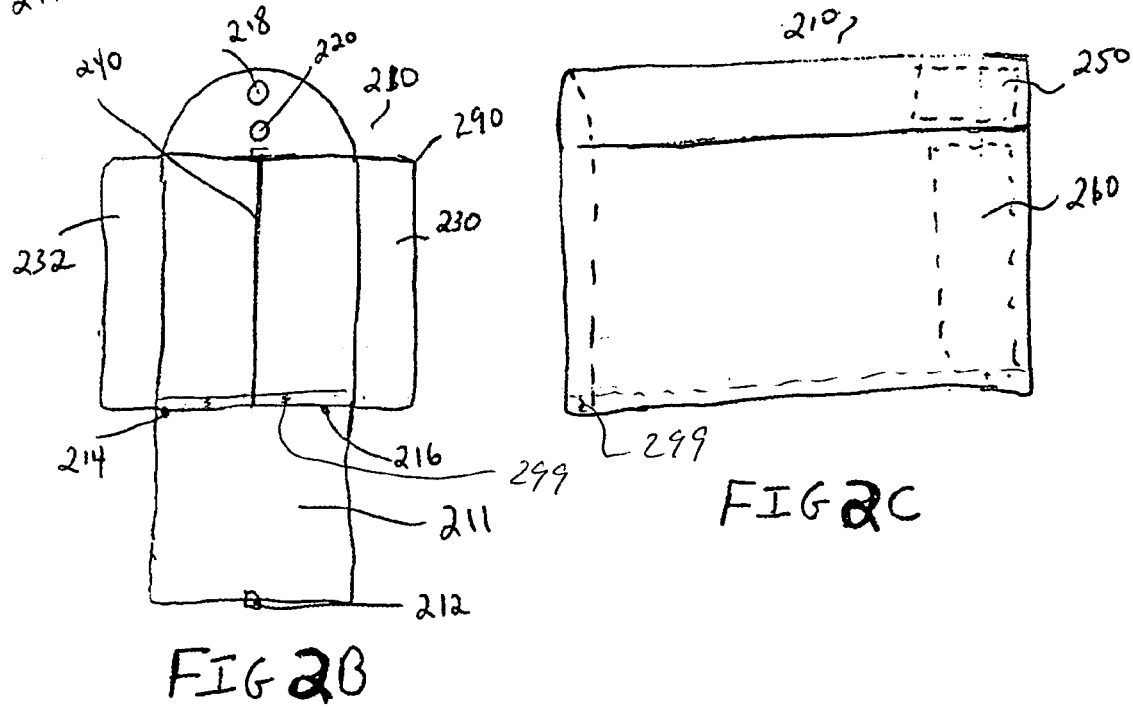
FIG 2B
FIG 2C

METHOD AND SYSTEM FOR DECONTAMINATING MAIL

BACKGROUND OF INVENTION

The embodiments described herein relate generally to decontaminating delivered items and more specifically to systems and methods for decontaminating mail during a relatively long period of time in a mailbox.

Anthrax spores have been detected on mail pieces, mail-handling equipment and in or near areas where certain mail pieces that likely contained anthrax were handled. Several people that were in such areas have contracted anthrax disease. These attacks pose a danger of infection that may be lethal to those in affected areas. Additionally, there is no warning system available to provide an early warning that a mail piece contains anthrax spores. Certain members of the general population may fear receiving and handling mail due to the threat of mail terrorism.

Anthrax is a biological agent that has apparently been placed in the U.S. postal delivery system in mail pieces that were camouflaged as ordinary mail and not properly marked or properly contained as a dangerous biological agent. The person placing such mail in the mail system had the apparent sole purpose of delivering the Anthrax as a biological weapon to kill the immediate victims and terrorize others who use the postal system. The Anthrax has apparently been transported in spore form and in such a small form as to float in the air.

The disease known as Anthrax disease is caused by the bacterium Bacillus anthracis that is known as Anthrax. Anthrax is rod-shaped, and relatively large for a bacterium at 1 to 10 µm in length.

The disease may be manifested as pulmonary anthrax or inhalation anthrax when a sufficient amount of Anthrax is inhaled. Such disease has been known as Woolsorter's Disease because Anthrax has been found in hoofed animals and the fur of such animals. Some people working with the fur have inhaled Anthrax.

The disease may be manifested as intestinal anthrax. Intestinal anthrax typically occurs when a person ingests undercooked infected meat. The disease may be manifested as cutaneous anthrax that is typically found when an open wound or sore of a person has been exposed to Anthrax.

Anthrax is a spore-forming bacterium such that it forms tough-shelled capsules known as spores that help it survive unfavorable conditions. The spores are a dormant form of the bacterium that can survive harsher conditions than the active bacterium and may survive in soil for many years. The spores may withstand a lack of moisture, certain amounts of radiation and some disinfectants. The spores may also survive in hotter or colder environments than the active bacterium.

If spores are introduced into a sufficiently warm and moist environment, such as inside a human body, they will then germinate and multiply. The typical hosts for Anthrax are animals, especially hoofed animals like cattle, sheep, goats and horses. Vaccination against Anthrax is not common except for those who are more likely to come in contact with it such as veterinarians and tannery workers.

Decontamination systems and methods have been used for water treatment, food sterilization and medical sterilization. Chlorine gas and chlorine dioxide gas have been used to disinfect sewage and control odor, but it is a poisonous gas. Chlorine gas is heavier than air and will remain close to the ground. Similarly, Ethylene Oxide is known to destroy anthrax spores.

Food sterilization equipment systems include high-energy heavy electron beam systems using electron accelerators, x-ray irradiation systems and gamma ray irradiation. Cobalt 60 is sometimes utilized as a source of radiation. Additionally, ultraviolet light radiation is sometimes utilized.

Biological and chemical weapon or hazardous material decontamination has been performed using liquid sprays, foams or fogs containing decontamination agents such as the Sandia National Laboratories Decon Formulation available from Modec, Inc. of Denver, Colo. and EnviroFoam Technologies, Inc. of Huntsville Ala. Such decontamination agents may not be effective against all contaminants and may or may not be toxic. Superheated steam is sometimes used in decontamination systems. Additionally, dry heat is also sometimes utilized, but is considered less effective than steam. Furthermore, ozone gas may be utilized in the proper conditions to neutralize anthrax spores.

Food and other decontamination systems require high throughput and fast processing times to be economically viable.

SUMMARY OF INVENTION

In one embodiment, a mail reception device includes a decontamination system and method to determine when to start decontamination. The decontamination system displays a decontamination process warning and begins the process. After a pre-determined amount of time, the system displays a decontamination-completed indication.

In another embodiment, a mailbox includes a system for determining if mail is present and a decontamination system that utilizes a lock to prevent a user from opening the mailbox before decontamination is complete.

In another embodiment, the mailbox includes a decontamination system that utilizes a remote messaging system to inform a user of the system status.

BRIEF DESCRIPTION OF DRAWINGS

FIG. 2A is a perspective view of a decontamination mailbox according to an embodiment of the present application.

FIG. 2B is a front view of a decontamination mailbox according to an embodiment of the present application.

FIG. 2C is a side view of a decontamination mailbox according to an embodiment of the present application.

DETAILED DESCRIPTION

Anthrax has been introduced into the mail system as a biological weapon. Similarly, other hazardous biological or chemical materials might be similarly transported in a mail system. Such criminal and terrorist activity provides a specific physical threat to mail recipients receiving contaminated mail and a general fear on the part of the general mail receiving public due to the potential danger in receiving and handling contaminated mail. There are many possible biological, chemical and other hazards that may be present in mail pieces.

The present application describes embodiments of a system and method for decontaminating mail. The embodiments are illustrative and where alternative elements are described, they are understood to fully describe alternative embodiments without repeating common elements of the other embodiments.

There are many forms and styles of residential mailboxes in use. In high-density housing locations such as apartment buildings, mailboxes are typically found in a mailbox room or alcove. In such buildings, a section of rows and columns of mailboxes are commonly accessed through a postal worker access door such that a single key allows access to the front panel that includes all of the individual mailbox doors. The postal worker then has access to the interior of each mailbox in the group. In a large mailbox room, there may be several such groups.

In medium-density housing locations, such as a townhouse development, mailboxes are typically found in a common mailbox area that may be outdoors. In medium-low-density housing locations, such as typical city and suburban neighborhoods with approximately 1/10-acre plots, mailboxes are typically found at each residence or a mail slot in a door is utilized.

In low-density housing locations, such as large plots off a small road that is near a rural road, mailboxes are typically found at a common area along side the rural road. In very-low-density housing locations, mailboxes are typically not available and the postal customer must retrieve mail from a post office box located at the post office.

Another popular mail reception facility is known as a private mailbox and is typically available at stores known as pack and ship stores. Such mailboxes may be available through vestibules that are open 24 hours per day using combination lock access to the vestibule area.

There are also several types of office mail delivery mailboxes in use. A department typically has a mail stop area with an open slot for each mail recipient. Alternatively, mail may be delivered to each office, cubicle or work area.

Figure 1A:
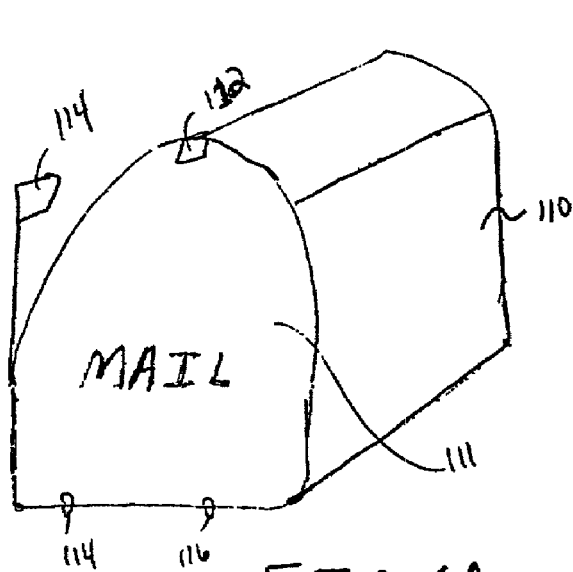
FIG. 1A is a perspective view of a prior art mailbox.
Figure 1B:
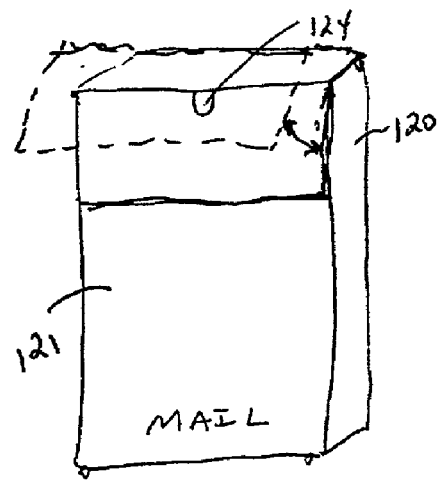
FIG. 1B is a perspective view of a prior art mailbox.
Figure 1C:
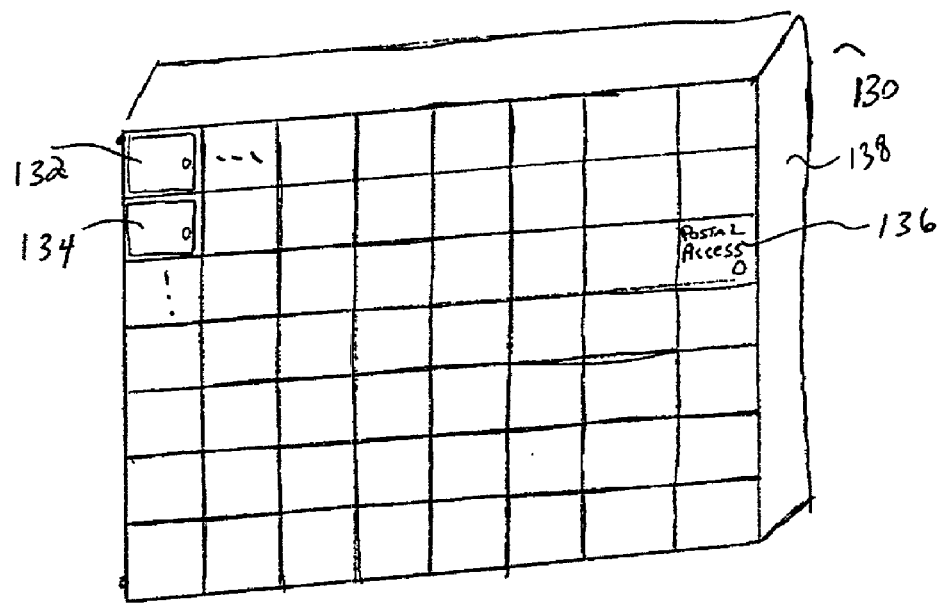
FIG. 1C is a partial perspective view of a prior art mail reception device including multiple mailboxes.

Referring to FIG. 1, prior art mailboxes are shown. They are typically used for residential mail reception. Referring to FIG. 1A, a typical post mount mailbox 110 is shown with a latch 112 to secure door 111 that has hinges 114, 116. An outgoing mail presence indicator 114 will alert the mail carrier to the presence of outgoing mail even if there was no incoming mail to deliver. The mailbox may be constructed from materials including steel and plastic. Referring to FIG. 1B, a typical house mount mailbox 120 is shown with door 121 and latch 124. Referring to FIG. 1C, a typical apartment building wall mount mailbox 130 is shown. The mailboxes 132, 134 have individual access keyed doors that are mounted in a frame 138 and includes a common access door that is opened by key access 136. Such apartment building units may include a single row of vertical mailboxes and may include an outgoing mail unit. They may also be mounted outside of a group of townhouses. The prior art mailbox units are not hermetically sealed and are not shielded.

Several illustrative embodiments are described below having varying complexity and that would entail varying costs. A heat-based system may provide a suitable solution whether based upon dry heat, steam or both. Similarly a gas or vapor system such as an ozone system may be utilized, as the byproducts of ozone are benign. Such systems may be able to operate without a perfectly hermetic seal. Similarly, chlorine gas or vapor may be utilized. Additionally, an antiseptic vapor may be utilized.

Additional systems are illustrated having additional complexity including radiation-based systems utilizing e-beam, x-ray and gamma ray systems. Additionally, poison gas systems using gasses such as chlorine dioxide or ethylene oxide could be utilized, but may require a hermetic seal and a purging system.

Figure 4A:
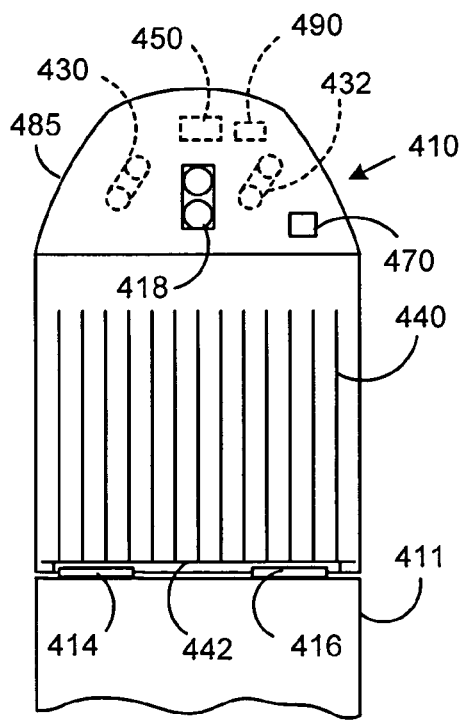
FIG. 4A is a partial view of a decontamination mailbox according to another embodiment of the present application.
Figure 4B:
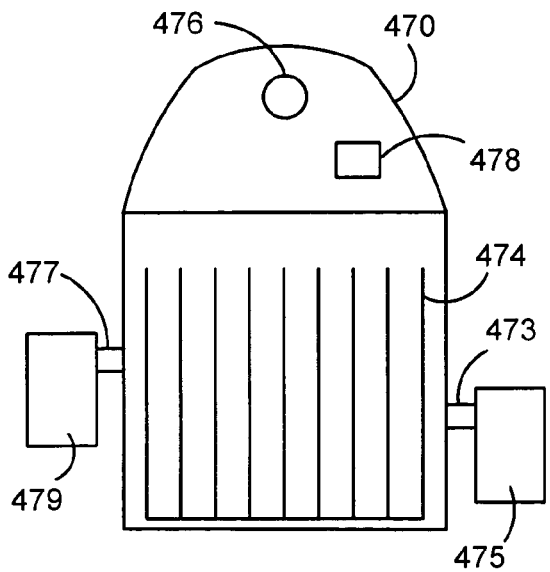
FIG. 4B is a front view of a decontamination mailbox according to another embodiment of the present application.
Figure 5:
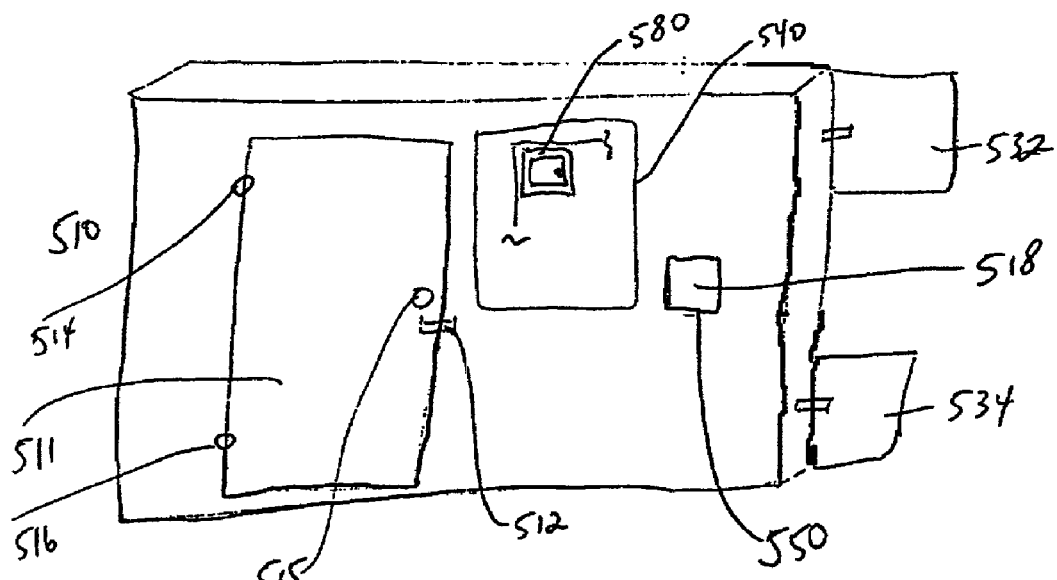
FIG. 5 is a perspective view of a decontamination mail reception room according to another embodiment of the present application.

Referring first to FIG. 4B, a gas based decontamination system is described. A more complex embodiment is described below with reference to FIG. 5. In this first embodiment, a mailbox that has a close to typical appearance is described incorporating a decontamination system. The mailbox includes an indicator system to provide an indicator as to when it is safe to open the mailbox. In this embodiment mailbox 470 has a door (not shown) with a latch (not shown). The interior of the mailbox includes a wire frame 474 elevated above the floor of the mailbox to separate mail pieces. Such separation will allow greater gas penetration.

Mailbox 470 includes a ozone generating system 475 which generates ozone gas and transmits it inside mailbox 470 via pipe 473. Alternately, ozone generation 475 could be located inside mailbox 470. A mail presence sensor (not shown) senses the presence of mail and sends a signal to a controller (not shown) which commands the ozone generation to generate ozone for a specified period of time. The ozone inside the mailbox displaces the air which exits the mailbox at exit vent 477. A hopcolyte filter 479 associated with the exit vent converts any escaping ozone to oxygen and water. Display features (not shown) display the status of the process to a user.

Alternatively, gas tube opening 476 is a receptacle for an ozone canister. A postal worker inserts mail into the frame 474 then closes the door. The postal worker inserts a canister that opens and releases the ozone gas. Indicator area 478 is an area that may be marked and later erased. In this embodiment, the postal worker writes in a time that it is safe to open the mailbox, two hours from when the postal worker inserted the ozone canister. The postal worker can then change the canister during the next mail delivery. In an alternative, the door will also open purge holes at the bottom of the mailbox when the door is opened to vent any byproduct water. In another alternative, the ozone canister opening is locked and a supply of canisters is stored at each home. In an alternative embodiment, the mailbox includes an ozone source. In an alternative, the mailbox is completely hermetically sealed when closed.

In an alternative, the ozone canisters are filled substantially near the time that they will be used.

Figure 3:
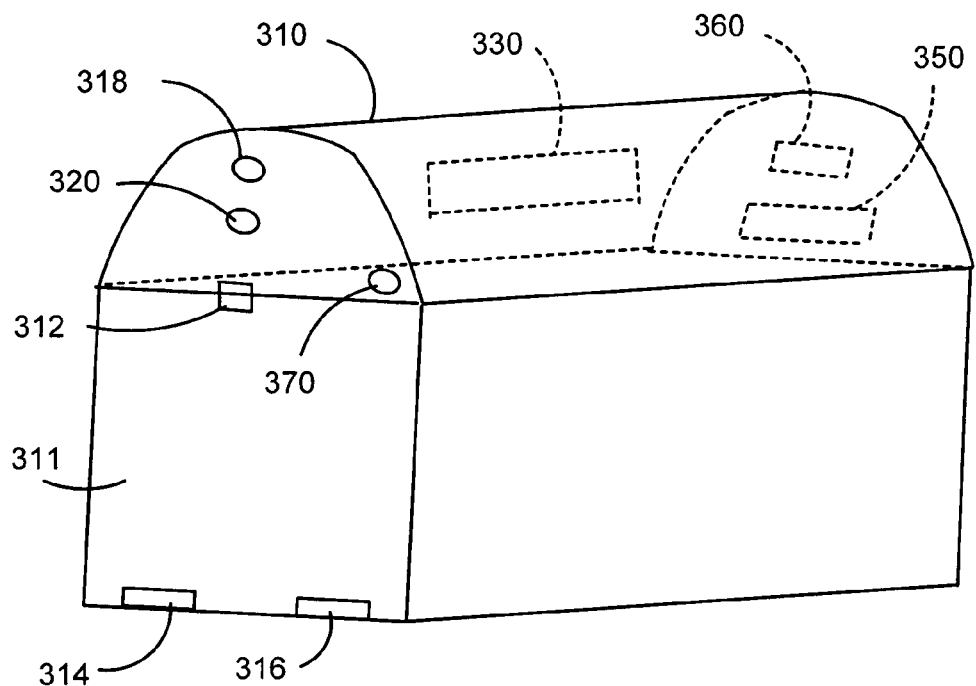
FIG. 3 is a perspective view of a decontamination mailbox according to another embodiment of the present application.

Referring to FIG. 3, another embodiment is described that utilizes a source of heat. Medical and dental equipment have been sterilized using superheated pressurized steam in equipment such as an autoclave. Both dry and wet heat systems have been used to sterilize medical equipment. However, it is desirable for such systems to operate at a very high throughput.

In this embodiment, the mailbox decontamination system includes a thermal process system such as a heating element to provide a thermal process in the range of about 260 degrees Fahrenheit to about 350 degrees Fahrenheit that corresponds to 131 degrees Celsius to 177 degrees Celsius. Thermal processes decontaminate bio-hazardous material at temperatures that are generally insufficient to cause chemical breakdown or to support combustion of paper fibers in mail.

The mailbox 310 includes an insulated oven interior for mail. The controller 350 is connected to a door switch to detect when the door is closed. The mailbox preferably includes an emergency off switch that turns off the system, even if it is performing a decontamination cycle. The mailbox includes a warning indicator 318 and a safe indicator 320. The mailbox also includes a start switch 370. The door 311 operates on hinges 314 and 316. Power source 360 is connected to the heat source 330 and the controller 350. In another embodiment, the mailbox contains a solenoid activated locking mechanism 312 that the controller uses to lock the mailbox 310.

The heating source 330 is preferably an electric resistive element and the control module contains a thermostat (not shown) connected to the controller. Other sensors such as infrared thermometers may be utilized. The control module 350 is programmable to allow all of the contents of a full mailbox to reach at least 131 degrees Celsius for a specified period of time such as 30 minutes. The controller 350 then turns off the heating element and waits until the thermometer measures a safe temperature to unlock the mailbox.

In an alternative embodiment, the mailbox is not locked, but a display including a warning light 318 notifies the user not to open the mailbox. Additionally, the mailbox contains vents and a fan that are utilized to cool the mailbox with outside ambient air after the decontamination cycle. The heat can be provided by conduction, natural or forced convection and/or thermal radiation including infrared heaters. The controller polls the thermometer to determine if the mailbox and mail has cooled down sufficiently to open the mailbox.

In an alternative embodiment, air is filtered by a HEPA filter before venting outside the mailbox.

In an alternative embodiment, the mailbox is brought to 200 or 300 degrees Fahrenheit for one hour, 250 or 350 degrees Fahrenheit for 30 minutes, or 320 degrees Fahrenheit for 120 minutes. In another alternative embodiment, the heating element includes a Peltier Effect electronics element that can also be utilized to cool down the mailbox after the decontamination cycle.

In another embodiment, superheated, pressurized steam is provided by the heating element 330. Wet heat steam systems are often utilized for medical device decontamination systems. In another embodiment, superheated, pressurized steam with very little relative humidity of 10% is utilized at 131 degrees Celsius. A humidity detector is connected to the controller and a pressure sensor is also connected to the controller. If a relative humidity detector is employed, the specific or absolute humidity value can be calculated.

Many types of industrial ovens and superheated steam systems are available and well know, so they are not described in detail.

In another embodiment, a mailbox that has a close to typical appearance is described incorporating a decontamination system with a start decontamination system and a safe to open determination and indication system. In an alternative, the mailbox includes a locking system that maintains a hermetic airtight seal until the safe to open determination system provides a signal indicating when it is safe to unlock the mailbox.

Referring to FIGS. 2A-2C, an embodiment of the present application is described. A mailbox 210 includes a decontamination system and status indication system 218, 220. The status indication system is connected to controller 250. The red LED 218 indicates it is not safe to open the mailbox and the green LED 220 indicates that it is safe to open. In one embodiment utilizing radiation, mailbox 210 is shielded to contain radiation by shield 290.

Food products including meat vegetables and spices have been treated with irradiation equipment in order to destroy bacteria and prolog the fresh life of the products. The equipment includes high-energy accelerated electron beam equipment, x-ray and gamma ray equipment, microwave energy sources, ultra-violet sources and other radiant energy sources. Food processing equipment typically operates x-rays at a maximum energy of 5 million electron volts and electron beams at a maximum of 10 million electron volts. Such electron beams can penetrate 35 inches of material having a density of 0.10 gram per cubic centimeter using double-sided irradiation. Typical systems include energy levels of 3 to 10 MeV with power ranges of 1 to 50 kW.

These procedures stress throughput and speed of operation. Anthrax bacteria, bacillus antrhracis, has been described as a very large, Gram-positive, spore-forming rod of 1-1.2 micron in width and 3-5 micron in length that form oval spores located centrally in a non-swollen sporangium. Typical paper has pores that average 10 microns in diameter. Thus, due to normal handling, some of the powdered anthrax spores which may be inside an envelope may easily move through the pores in the envelope and enter the air or adhere to the external surface of a mail piece.

High energy ionizing electron beam and x-ray equipment may destroy bacteria DNA rendering such bacteria harmless by killing them or rendering them incapable of multiplying. However, such devices may destroy electronic circuits, photographic prints, film, seeds and prescription drugs. Such equipment may also discolor glass. High-energy electron beams may penetrate around one-foot thick materials and x-ray equipment could penetrate thicker material including material several feet thick. Additionally, gamma ray equipment such as those utilizing a radioactive Cobalt-60 source, a radioactive Cesium-137 source or other material may be utilized. Such systems require extensive shielding systems such as thick concrete walls. Spores generally require a significantly greater radiation dose than non-spore bacteria. If a logarithmic D-value kill scale is used, a 4D dose will kill 99.99% of the target. Food may typically be irradiated at 1.2 kiloGray (120,000 rad), but spores may require as much as 11 or 50 kiloGray for a 4D dose. Accordingly a dose of 5.6 million rads may be sufficient to render anthrax spores harmless. This dosage can be delivered over a longer period of time using substantially lower powered electron beams that are produced using less costly equipment.

Mailbox 210 is preferably airtight when closed. The postal worker opens door 211 using latch 212. The door opens on hinges 214, 216. The controller 250 includes a mail presence sensor such as a light beam system or spring biased switch 299 to detect the presence of mail. When the mailbox is opened, mail is inserted and the mailbox closed, the controller 250 starts a decontamination cycle. The controller lights warning LED 218. The controller initiates radiation sources 230, 232. In this embodiment, the sources include an electron gun to provide 300 KeV soft electrons. The beams sweep through each side of the mailbox using deflector coils against a backstop 240 that will absorb the beam and not produce x-rays. The backstop 240 may include a heat sink to the exterior of the mailbox.

The beams sweep the contents until the required radiation dose is delivered. For example, the system is powered by power source 260 and provides 3-kilowatt beams for six hours. After the decontamination cycle is completed the safe light 220 is lit and the warning light 218 is turned off. Other decontamination cycles may be used.

In another embodiment, a single radiation source is utilized and the controller 250 will utilize a pressure sensor to monitor the mailbox interior pressure and shut down the radiation source if a dangerous pressure such as 5 atmospheres exists. In an additional embodiment, a pressure valve will vent the mailbox if dangerous pressures are reached in the mailbox interior. In another embodiment, each radiation source contains four electron guns and deflectors, the controller allows a cool down period to dissipate any excess heat built up in the mail pieces and the controller locks the mailbox latch during the decontamination process.

In a further embodiment hard electron sources as described above are utilized for radiation sources 230, 232. The may include 3 MeV units at 25 kilowatts. Electron beam equipment standards may be found in ANSI/AAMI/ISO 11137 (1994) and EN 552. Dry heat sterilization and steam sterilization parameters may be found in AAMI ST-50 (1995) and ANSI/AAMI/ISO 11134 (1995). An anthrax spore brought to approximately 131 degrees Celsius should be neutralized in a relatively short period of time on the order of several minutes.

In an additional embodiment, a microwave energy source is utilized for radiation sources 230, 232. Commonly available magnetrons produce microwave energy at 2.45 GHz because that frequency is a standard frequency selected for conventional microwave ovens. The standard frequency allows reasonable energy penetration into foods at a reasonable energy absorption in water. A standard frequency allows communications systems to avoid any interference from ovens based upon that frequency. In another embodiment, a metal detector or microwave reflective substance detector would automatically disable the microwave source and warn the user that the decontamination cycle has not taken place.

In another embodiment, the magnetron is slidably fixed to a guide rail and moved in one axis to vary the "hot spots" of the device. In a further embodiment, a Variable Frequency Microwave (VFM) microwave energy source is utilized. Such a source preferably varies frequency at an effective absorption frequency range for anthrax spores and such that the unit may process metal and reflective materials. In an additional embodiment, a single mode 915 MHz microwave oven is utilized. A 915 MHz source will penetrate articles to greater depths than a 2.45 GHz source. Microwave source and shielding systems and methods are known and not described in detail in this application.

Controllers and timers are well known and not described in detail. The processes described may be performed in hardware, firmware, in software on a general-purpose processor or combination thereof. The controller may be an 8052 micro controller and support circuits, but may include a more powerful processor and may be re-configurable and may be networked via a wired or wireless communications channel.

Referring to FIG. 4A, another embodiment is described. Ultra violet (UV) light, particularly the light in the UV C spectrum is narrow wavelength light that is effective at killing bacteria on surfaces. Anthrax has been transported on the surface of envelopes. A mailbox 410 includes a controller 450 that may even be mechanical. UV C radiation sources at 260 nm 430, 432 are connected to a controller 450. The controller 450 is connected to a decontamination start switch 470, a timer and a display 418. The mailbox 410 is shielded 485 to prevent UV C radiation from escaping and is reflective. The mailbox interior has dividers 440 that allow the UV C energy to bathe the surfaces of each mail piece placed in each of the slots created by dividers 440. Divider bottom 442 is at least partially transparent to UV and allows UV C energy to bathe the bottom surfaces of the mail pieces. The postal worker places the mail in the mailbox, closing the door 411 having hinges 414, 416. The postal worker uses a key to turn the switch 470 to start the decontamination and the postal worker leaves. The display 418 displays a warning and the door is locked. The UV C lights are lit for a predetermined time such as three hours and provide at least 20 milliwatts per centimeter squared of 260-nanometer light. One or 5 hours may be utilized, however, other time periods may be effective. The mailbox may utilize a communications channel and communications device 490 to provide an indication inside a home.

After the predetermined time expires, the door 411 is unlocked and the display indicates it is safe to open the door and retrieve the mail. In an alternative, this system is used along with a microwave system described above.

In an alternative, there is no display, but the mailbox is locked until the cycle is complete. The decontamination cycle start indicator may be a push button switch or a mail presence indicator such as a spring-loaded switch.

Referring to FIG. 5, an embodiment showing a group mailbox is described. Mailroom 510 includes an airtight compartment with a door 511 on hinges 514, 516 with handle 515 and bolt lock 512. Window 540 allows users to view the interior including the racks of individual mailboxes 580. Controller 550 includes a display 518 and keyboard for the entry of commands and passwords or codes. Sterilizing gas supply 532 is connected to the mailroom interior as is evacuator/scrubber 534. In one embodiment, an ozone source is utilized and a filter such as Hopcolyte is required to convert remaining ozone into benign byproducts of oxygen and water after the sterilizing is complete.

Certain chemicals compounds or diluted portions of such compounds including the gaseous forms of such compounds have been used to neutralize bacteria including cetypyridinium chloride, chlorine, chlorine gas and ozone. Household chlorine bleach may be an effective sterilization agent if applied in gaseous form. Chlorine gas may be utilized. Alternatively, chlorine dioxide gas may be used. Chlorine dioxide may be produced several methods including the use of generation systems such as those available from Severn Trent Services, Inc. of Colmar, Pa. and chlorine dioxide releasing powder available from Engelhard Corporation of Iselin, N.J.

The postal worker enters a pass code and the lock is opened. The postal worker loads the individual mailboxes 580 as conventionally done. The postal worker exits, closes the door and presses a start decontamination button. Alternatively, the postal worker enters a start decontamination code or uses a key to activate a switch to start the cycle. The system preferably encloses the bank of mailboxes. However, the system may alternatively encompass the entire mailroom. Such a system uses thermal, motion, sound, and light beam detectors to determine the mailroom 510 is empty. The controller locks the room and then starts decontamination by using chlorine gas for two hours. The controller activates; evacuator/scrubber 534 to clean the room. A purging system may be utilized. The system then tests the environment using a chlorine gas detector. If clear, the controller unlocks the door 511 and allows user access.

A chlorine dioxide sensor such as those available from CEA Instruments, Inc., Emerson, N.J. may be utilized to determine when to signal that it is safe to open the mailbox. The system may filter the chlorine dioxide through an ascorbic bath to inactivate the gas. Vapor scrubber equipment such as that available from USFilter of Warrendale, Pa. may be utilized.

In an alternative embodiment, the chlorine dioxide gas is introduced at a pressure higher than atmospheric such as 1, 2 or 3 atmospheres of pressure. Additionally, the gas may be heated to above ambient temperature to 100, 150 or 200 degrees Fahrenheit.

Figure 6:
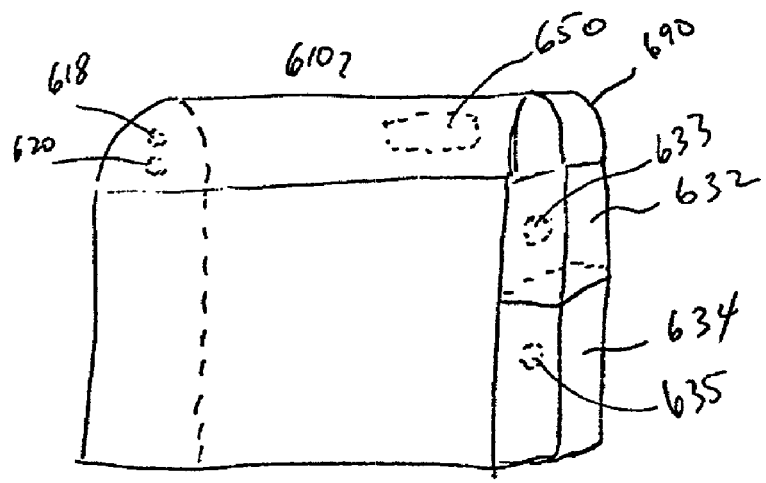
FIG. 6 is a perspective view of a decontamination mailbox according to another embodiment of the present application.

Referring to FIG. 6, another embodiment is described. Mailbox 610 is sealed when closed. Indicators 618 and 620 provide warning and clear indications as above. Controller 650 is powered (not shown) and connected to plumbing (not shown) to control allowing source decontaminant gas (chlorine dioxide or ozone) from 632 to enter the mailbox through opening 633. The controller 650 receives a start decontamination cycle indication, the gas is applied and after a set period of time (2 hours) is evacuated through 635 to 634. The mailbox is then unlocked and a safe indication given. In an alternative embodiment, the postal worker uses a key access and the gas subsystem 690 is removable for service by the user or if required by an authorized maintenance technician. Alternatively, the mailbox is hermetically sealed when closed.

As can be appreciated, a mechanism can be employed to open a cap of a container having vapor producing liquid and to close the cap after a specified time. Additionally, an aerosol and atomizing mechanism can be employed to release vapor into the enclosed atmosphere of the mailbox for a specified period of time. The system will saturate the atmosphere inside the enclosed space of the mailbox and the enclosed mail pieces will soak in the atmosphere for a desired period of time such as 2 hours. Paper is generally porous and humidity alone can increase the percent of water in the paper inside an envelope within a relatively short period of time of about 5 to 30 minutes. Similarly, the sterilizing or antiseptic vapor will permeate and saturate the envelopes in the mailbox over time such that any bacteria in or on the envelopes will be killed or rendered harmless by the vapor.

In an alternative embodiment, an ozone system may be utilized including those available from Bioquell Food of Andover, Hampshire, England. Ozone of at least 9000 ppm may be used for at least 70 minutes in one embodiment.

In another alternative embodiment, decontamination foam systems Modec Inc. of Denver Colo., developed by Sandia National Laboratories of Albuquerque, N. Mex. may be utilized. The foam is pumped into the mailbox and the mail pieces are soaked in the foam for a specified period of time. Pressure and heat may additionally be supplied to aid the foam in permeating through the mail pieces. After a period of time such as 4 hours, the system is evacuated to remove residual foam and the mailbox is then opened.

Figure 7:
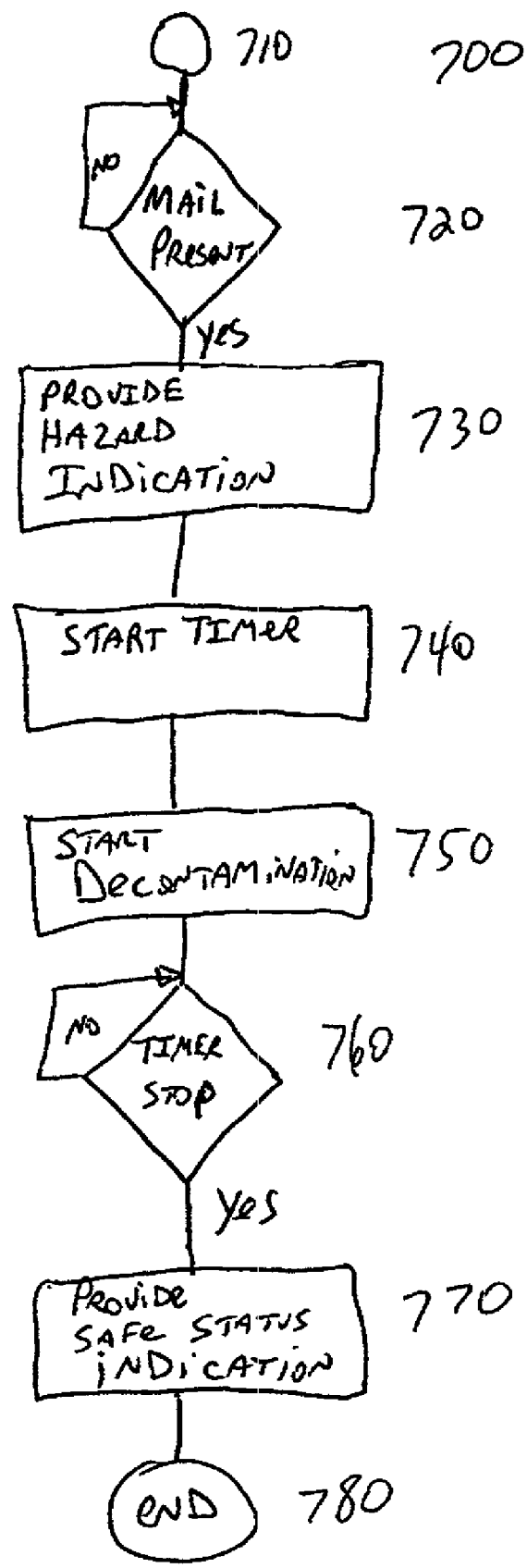
FIG. 7 is a flowchart showing the decontamination process according to another embodiment of the present application.

Referring to FIG. 7, a process 700 for decontaminating mail in a mailbox is described. The process starts in step 710. In step 720, the processor receives an indication that mail pieces have been placed in the mailbox. In step 730, the system provides a hazard indication such as lighting a red LED. In step 740, the system starts the decontamination timer for a pre-selected period of time such as two hours. In step 750, the system begins the decontamination cycle, such as by utilizing dry heat to have all mail pieces in the mailbox reach a constant temperature of at least 160 degrees Celsius.

In step 760, the system checks the timer to see if the timer has completed counting down. After the predetermined length of time, the system proceeds to step 770 to provide a safe indication such as by lighting a green LED and extinguishing the red LED. The process then ends in step 780. In an alternative embodiment, step 720 the processor receives a start decontamination request from a user via a start code, button or switch. Alternative additional steps include activating a lock as part of step 730 and deactivating the lock as part of step 770.

As discussed above, several modifications to the process are possible. For example, the mailbox may utilize a communications channel and communications device to provide an indication inside a home in step 720 that "the mail has arrived" followed in step 750 by an indication that "the mail is being sanitized" and then followed in step 770 by an indication that "it is now safe to pick up and open your mail." Similarly, for the embodiments that use a sanitizing compound, the communications device may be utilized to provide an indication that "it is time to replace the compound." The above specification describes system and methods for decontaminating mail. As can be appreciated, various combinations of the above decontamination systems may be utilized in a single mailbox using one or more controllers. In an alternative, the decontamination systems described may be incorporated into a group mailbox.

The described embodiments are illustrative and the above description may indicate to those skilled in the art additional ways in which the principles of this invention may be used without departing from the spirit of the invention. Accordingly the scope of the claims should not be limited by the particular embodiments described.

The invention claimed is:

1. A mailbox for decontaminating mail comprising:
   the mailbox defining an interior for receiving mail;
   a door for allowing access to the interior of the mailbox;
   a decontamination system operatively connected to a controller for decontaminating mail;
   at least one divider positioned in the interior of mailbox for separating mail; and
   a keyed start switch that is engaged and switched to start when a key is inserted and turned in the keyed start switch and that is used to send a decontamination start signal to the decontamination system and to restrict decontamination start signal generation to a mail carrier possessing the key.

2. The mailbox of claim 1, wherein
   the controller includes a communications device for providing status information to a remote user located inside a home.

3. The mailbox of claim 2 wherein:
   the communications device includes a wireless network communications channel.

4. The mailbox of claim 3 wherein:
   the communications device is configured to provide an indication to the remote user indicating that the mail has arrived and then provide an indication to the remote user indicating that a decontamination process is underway.

5. The mailbox of claim 1 further comprising:
   reflective shielding operatively connected to the mailbox to prevent UV radiation from escaping.

6. The mailbox of claim 1 wherein:
   the divider material is at least partially transparent to UV radiation.

7. A mailbox device including a decontamination chamber comprising:
- a door for allowing access to the interior of the decontamination chamber;
- a decontamination system operatively connected to a controller for decontaminating mail;
- at least one divider positioned in the interior of the decontamination chamber for separating mail; and
- a keyed start switch that is engaged and switched to start when a key is inserted and turned in the keyed start switch and that is used to send a decontamination start signal to the decontamination system and to restrict decontamination start signal generation to a mail carrier possessing the key.

8. The mailbox of claim 7 wherein:
the decontamination system includes a UV source; and
the divider material is at least partially transparent to UV radiation.

9. The mailbox of claim 7 further comprising:
a communications device for providing status information to a remote user located inside a home and wherein the communications device is configured to provide an indication to the remote user indicating that the mail has arrived and then provide an indication to the remote user indicating that a decontamination process is underway.

10. A mailbox for decontaminating mail comprising the mailbox defining an interior for receiving mail:
- positioned in the interior of the mailbox;
- a door for allowing access to the interior of the mailbox;
- a decontamination system including a UV source operatively connected to a controller for decontaminating mail;
- reflective shielding operatively connected to the mailbox to prevent UV radiation from escaping;
- at least one divider positioned in the interior of the mailbox for separating mail and including divider material that is at least partially transparent to UV radiation; and
- a keyed start switch that is engaged and switched to start when a key is inserted and turned in the keyed start switch and that is used to send a decontamination start signal to the decontamination system and to restrict decontamination start signal generation to a mail carrier possessing the key.

\* \* \* \* \*